United States Patent
Kraft et al.

(10) Patent No.: US 9,164,183 B2
(45) Date of Patent: Oct. 20, 2015

(54) METHOD FOR DETECTING X-RAY RADIATION AND DETECTOR SYSTEM WITH DIRECT CONVERSION DETECTORS

(75) Inventors: Edgar Kraft, Erlangen (DE); Daniel Niederlöhner, Erlangen (DE); Christian Schröter, Bamberg (DE)

(73) Assignee: SIEMENS AKTIENGESELLCHAFT, Munich (DE)

( * ) Notice: Subject to any disclaimer, the term of this patent is extended or adjusted under 35 U.S.C. 154(b) by 427 days.

(21) Appl. No.: 13/419,461

(22) Filed: Mar. 14, 2012

(65) Prior Publication Data
US 2012/0235052 A1 Sep. 20, 2012

(30) Foreign Application Priority Data

Mar. 15, 2011 (DE) .......................... 10 2011 005 539

(51) Int. Cl.
| | | |
|---|---|---|
| *G01J 1/42* | (2006.01) | |
| *G01T 1/00* | (2006.01) | |
| *G01T 1/40* | (2006.01) | |
| *G01T 1/17* | (2006.01) | |
| *A61B 6/00* | (2006.01) | |
| *A61B 6/03* | (2006.01) | |
| *G01T 1/24* | (2006.01) | |

(52) U.S. Cl.
CPC . *G01T 1/40* (2013.01); *A61B 6/032* (2013.01); *A61B 6/4241* (2013.01); *A61B 6/482* (2013.01); *G01T 1/17* (2013.01); *G01T 1/247* (2013.01)

(58) Field of Classification Search
USPC ........................................................ 250/394
See application file for complete search history.

(56) References Cited

U.S. PATENT DOCUMENTS

| | | | |
|---|---|---|---|
| 3,435,220 A * | 3/1969 | Hanken | ........................... 378/53 |
| 5,943,388 A | 8/1999 | Tümer | |
| 7,518,118 B2 | 4/2009 | Harrison et al. | |
| 2005/0167606 A1 | 8/2005 | Harrison et al. | |
| 2008/0203313 A1 | 8/2008 | Cook | |
| 2008/0267353 A1* | 10/2008 | Rundle | ........................... 378/87 |
| 2009/0194703 A1* | 8/2009 | Eversmann et al. | .......... 250/395 |
| 2009/0304149 A1 | 12/2009 | Herrmann et al. | |
| 2009/0310736 A1* | 12/2009 | Ziegler et al. | ...................... 378/5 |

(Continued)

FOREIGN PATENT DOCUMENTS

| | | |
|---|---|---|
| CN | 101228437 A | 7/2008 |
| DE | 102008005373 A1 | 7/2009 |

OTHER PUBLICATIONS

German Office Action for German Application No. 10 2011 005 539.8 (Not Yet Published).

(Continued)

*Primary Examiner* — Christine Sung
(74) *Attorney, Agent, or Firm* — Harness, Dickey & Pierce, P.L.C.

(57) ABSTRACT

A method and a detector system are disclosed for the photon-counting detection of x-ray radiation with direct conversion detectors. In at least one embodiment of the method, as a function of the existing radiation energy, current and/or voltage pulses which are largely proportional thereto are generated, and the generated current and voltage pulses are counted in the detector when a predetermined current and/or voltage source is exceeded, whereby a threshold is used as a predetermined current and/or voltage threshold, which corresponds to a detection of a photon with an energy which is less than the k-edge of the detector material used.

20 Claims, 2 Drawing Sheets

(56) References Cited

U.S. PATENT DOCUMENTS

| | | | | |
|---|---|---|---|---|
| 2010/0187432 | A1* | 7/2010 | Herrmann et al. | 250/395 |
| 2010/0270473 | A1* | 10/2010 | Kraft et al. | 250/389 |
| 2011/0012014 | A1* | 1/2011 | Livne et al. | 250/252.1 |
| 2011/0096905 | A1* | 4/2011 | Roessl et al. | 378/62 |
| 2011/0233394 | A1* | 9/2011 | Glasser et al. | 250/252.1 |
| 2011/0311022 | A1* | 12/2011 | Kappler | 378/19 |
| 2012/0087463 | A1* | 4/2012 | Greenberg et al. | 378/5 |
| 2012/0235052 | A1* | 9/2012 | Kraft et al. | 250/394 |

OTHER PUBLICATIONS

Certified German Priority document for German Application No. 10 2011 005 539.8 (Not Yet Published).

1 Chinese Office Action and English translation thereof dated Jan. 28, 2014.

* cited by examiner

METHOD FOR DETECTING X-RAY RADIATION AND DETECTOR SYSTEM WITH DIRECT CONVERSION DETECTORS

PRIORITY STATEMENT

The present application hereby claims priority under 35 U.S.C. §119 to German patent application number DE 10 2011 005 539.8 filed Mar. 15, 2011, the entire contents of which are hereby incorporated herein by reference.

FIELD

At least one embodiment of the invention generally relates to a method for the photon-counting detection of x-ray radiation with direct conversion detectors within the field of medical or material examination CT systems. At least one embodiment is more specifically directed to a method wherein includes whereby as a function of the existing radiation energy, current and/or voltage pulses which are largely proportional hereto are generated and the generated current and/or voltage pulses are counted in the detector when a current and/or voltage threshold has been exceeded. Furthermore, at least one embodiment of the invention also generally relates to a detector system for the photon-counting detection of x-ray radiation with direct conversion detector elements according to at least one embodiment of the method.

BACKGROUND

Methods and detectors are generally known. The dose rate and also the energy distribution of a detected radiation are herewith measured by free charges developing in a detector material on account of the ionizing radiation being measured as current or voltage pulses. The extent of a thus developing charge pulse is approximately proportional here to energy of the x-ray quantum and/or photons which penetrate the detector material in each instance. During the measurement of such events, care is generally taken to ensure that the existing noise is always suppressed as much as possible in the electronic measuring equipment, by a threshold being switched, which has to be exceeded before a pulse is counted. Since within the scope of measurements within the field of medical or material examination CT systems, x-ray radiation spectra in the energy range from 30 keV to generally less than 300 keV are generally used, these threshold values are set such that they do not lie significantly below the equivalent of 30 keV. An adequate noise range is herewith ensured.

It has been shown that methods and detectors of this type comprise a relatively strong drift with respect to their radiation sensitivity and as a result lead to incorrect measurement results.

SUMMARY

At least one embodiment of the invention is directed to a method for the photon-counting detection of x-ray radiation with direct conversion detectors in the field of medical or material examination CT systems and/or a detector system used herefor which is less prone to drift.

The inventors propose at least one embodiment of a method for the photon-counting detection of x-ray radiation using direct conversion detectors, whereby:

as a function of the existing radiation energy, current and/or voltage pulses which are largely proportional hereto are generated and the generated current and/or voltage pulses are counted in the detector when a predetermined current and/or voltage threshold is exceeded, and a threshold is used as a predetermined current and/or voltage threshold, which corresponds to a detection of a photon with an energy, which is lower than the k-edge of the detector material used.

Within the scope of at least one embodiment of the invention, a detector system is also proposed for the photon-counting detection of x-ray radiation with direct conversion detector elements, whereby the detector elements and their evaluation electronics systems are to be embodied such that the afore-described inventive method is executed.

Advantageous developments of the invention form the subject matter of the subordinate claims.

BRIEF DESCRIPTION OF THE DRAWINGS

The invention is described in more detail below with the aid of the figures, whereby only the features needed to understand embodiments of the invention are shown. The following reference characters are used: 1: CT system; 2: first radiation source; 3: first detector; 4: second radiation source; 5: second detector; 6: gantry housing; 7: patient; 8: patient couch; 9: system axis; 10: computing station; E: counted result; K: continuous pulse height discriminator; L: logic element; Prg1-Prgn: computer programs; S: pulse shaper; T: clocked pulse height discriminator; V: amplifier.

The figures show in detail

Figure 1:
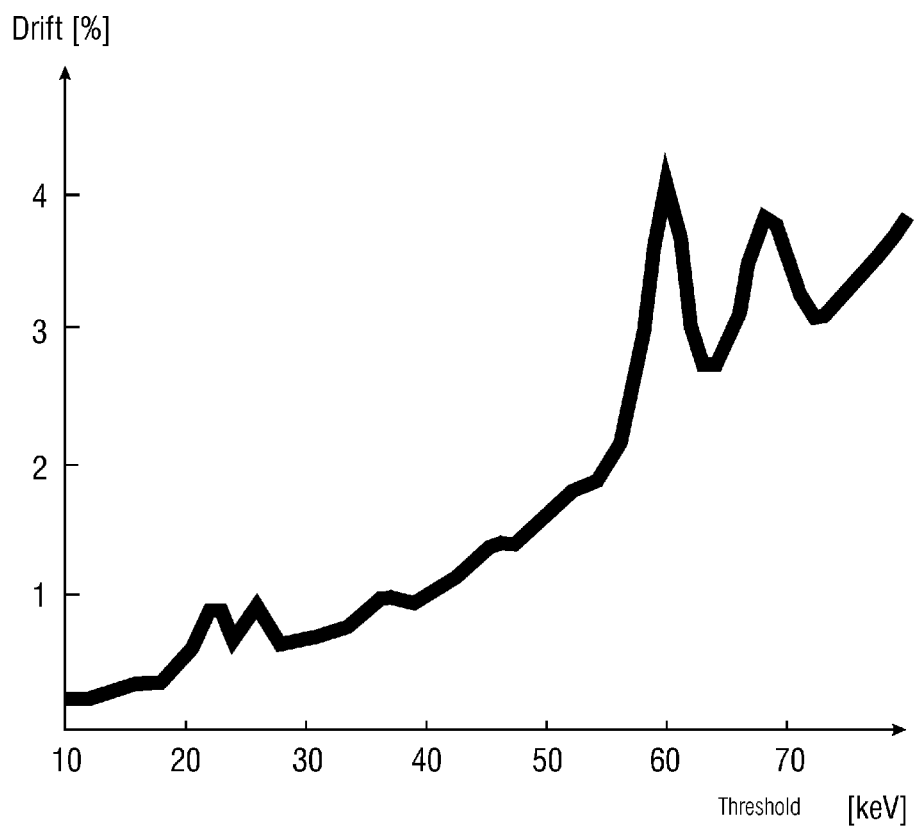
FIG. 1 a dependency of the count rate drift on the set threshold value.

It should be noted that these Figures are intended to illustrate the general characteristics of methods, structure and/or materials utilized in certain example embodiments and to supplement the written description provided below. These drawings are not, however, to scale and may not precisely reflect the precise structural or performance characteristics of any given embodiment, and should not be interpreted as defining or limiting the range of values or properties encompassed by example embodiments. For example, the relative thicknesses and positioning of molecules, layers, regions and/or structural elements may be reduced or exaggerated for clarity. The use of similar or identical reference numbers in the various drawings is intended to indicate the presence of a similar or identical element or feature.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Before discussing example embodiments in more detail, it is noted that some example embodiments are described as processes or methods depicted as flowcharts. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Methods discussed below, some of which are illustrated by the flow charts, may be implemented by hardware, software, firmware, middleware, microcode, hardware description languages, or any combination thereof. When implemented in software, firmware, middleware or microcode, the program code or code segments to perform the necessary tasks will be stored in a machine or computer readable medium such as a storage medium or non-transitory computer readable medium. A processor(s) will perform the necessary tasks.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

In the following description, illustrative embodiments may be described with reference to acts and symbolic representations of operations (e.g., in the form of flowcharts) that may be implemented as program modules or functional processes include routines, programs, objects, components, data structures, etc., that perform particular tasks or implement particular abstract data types and may be implemented using existing hardware at existing network elements. Such existing hardware may include one or more Central Processing Units (CPUs), digital signal processors (DSPs), application-specific-integrated-circuits, field programmable gate arrays (FPGAs) computers or the like.

Note also that the software implemented aspects of the example embodiments may be typically encoded on some form of program storage medium or implemented over some type of transmission medium. The program storage medium (e.g., non-transitory storage medium) may be magnetic (e.g., a floppy disk or a hard drive) or optical (e.g., a compact disk read only memory, or "CD ROM"), and may be read only or random access. Similarly, the transmission medium may be twisted wire pairs, coaxial cable, optical fiber, or some other suitable transmission medium known to the art. The example embodiments not limited by these aspects of any given implementation.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

For the detection of gamma and x-ray radiation, in particular in CT (computed tomography) and dual energy CT, direct conversion detectors based on semi-conductive materials such as for instance CdTe, CdZnTe, CdZnTeSe, CdTeSe, CdMnTe, InP, TlBr2, HgI2 are used. With these detectors, individual x-ray quanta are counted instead of an integrated signal. The measured value which contributes to the imaging, is therefore a count rate. The count rate is detected by an electronics system, which always then detects an event if the current pulse resolved by the x-ray quantum exceeds a certain threshold value. The extent of this threshold value may be calibrated on the detected x-ray energies and is therefore typically specified in keV.

A developing polarization particularly in the case of a flux density of the radiation which is needed for CT devices is common to the said materials. This is caused by an increased allocation of interference points under flux and thus increased recombination. This results in a reduction in the collected charge quantity per x-ray quantum and thus in a smaller amplitude of the current pulse.

In the polarized state, several pulses therefore now fail to meet the threshold value and do not trigger any counter event. This therefore results in a reduction in the measurement signal on account of the polarization. This phenomenon is referred to as "detector drift" or in short "drift".

In conjunction with imaging methods and a reconstruction of image data from detector data which is implemented in this way, such a drift of the detectors results in various image artifacts and a quantitative measurement of absorption values from image data reconstructed in this way barely being possible anymore. It is therefore proposed to use as low-noise an electronics system as possible, which enables measurement in the case of particularly low thresholds. The measuring threshold may therefore be set very low, on the other hand still with an adequate noise level range. The reason as to why this solution intensifies the drift problem is that a material-imminent drift is clearly less significant with low thresholds than with high thresholds. Sufficiently low drift values are achieved with a threshold energy of 20 keV, better 10 keV, better 5 keV.

The lower limit for the adjustable threshold represents the noise level of the amplifier. This noise level approximately follows a Gaussian distribution, the width of which is determined by the electronic noise and the absolute degree of which is determined by the bandwidth and/or maximum rate of the analog processing chain. The threshold must therefore be set at least so high that the noise-generated counter events (dark count rate) do not negatively influence the imaging. This is then the case if the dark count rate is significantly lower than the minimum flux to be detected. In computed tomography, the maximum flux lies at approximately $1 \times 10^9$ quanta/(mm2*s). The dynamic range amounts to six orders of magnitude. A dark count rate of a maximum of approximately $1 \times 10^3$ quanta/(mm2*s) is therefore acceptable.

The noise level of the amplifier should therefore be provided such that this dark count rate is not exceeded with the threshold energy set for drift minimization. This requirement proceeds in part contrary to the desire whereby signal processing electronics systems can temporarily process very tight pulse sequences. For a given field of application, aside from a careful noise optimization, individual consideration should therefore be given to the achievable speed and the minimum threshold setting.

In order to reduce or even minimize the noise of the signal processing chain, all current methods can basically be used. Particularly favorable methods of example embodiments are for instance:
  reducing or even minimizing the input capacitance of the preamplifier caused by the detector electrodes and their connection;
  adjusting the feedback capacitance of the preamplifier to the detector input capacitance;
  careful optimization of the preamplifier as a dominant noise source;
  improving or even optimizing the transmission function of the signal chain to the signal and noise output spectrum;
  improving or even maximizing the time constant of the chopper (=maximizing the shaping time) to costs of the maximum count rate;
  reducing the digital-to-analog crosstalk, by maximal spatial and electronic separation of the digital and analog part and reducing or even minimizing the sensor leakage current.

Furthermore, it is favorable to use particularly suitable calibration methods for drift minimization. While the electronic noise determines the lowest adjustable threshold of a pixel, with a plurality of pixel-generating detector elements on the detector, the variation of noise should also be taken into account between the individual pixels (dispersion) and the adjustability of the thresholds (DAC resolution, DAC stepwise and DAC adjustment range). A drift-minimized detector should therefore also feature an apparatus for adjusting the threshold, which is adjusted to the dispersion of the pixel and to the required energy resolution.

In accordance with at least one embodiment of the invention, two particularly advantageous embodiment variants are proposed with different preference during the threshold calibration:

a) If the energy resolution of the detector is of significant interest, it is therefore advantageous to set the individual pixels of the detector, in more precise terms the pixel-generating detector elements to as identical a threshold as possible. In this case, the minimal threshold is not only determined by the electronic noise, but instead also by its dispersion between the pixels. A drift-optimized detector of this type is subsequently also characterized by a dispersion-optimized design according to the current method. This means that the deviation of the noise level from pixel to pixel is to be minimal and the threshold should therefore also be set identically across the whole detector.

b) If the main requirement is the lowest possible drift, the minimal threshold can be set in a pixel-individual fashion at the cost of energy resolution such that the required maximum dark count rate is not met. The dispersion of the signal-processing electronics system translates in this case into an energy dispersion of the threshold. An automatic method is possible here for instance as a calibration mechanism, which measures the dark count rate with each threshold setting and sets the energy threshold in each pixel to the lowest value which fulfills the dark count rate criteria.

Irrespective of the choice of the type of threshold setting, it may naturally be advantageous to provide higher energy thresholds in the pixels. It may also be advantageous to link or correct the signal thereof with the signal of the low drift threshold.

At least one example embodiment achieves a reduction and/or elimination of the detector drift, a high quanta efficiency results from the detection of all signal pulses generated by x-ray quanta and a good energy resolution is achieved by a low-noise electronics system, which produces a particularly high contrast with dual energy CT examinations.

The inventors propose at least one embodiment of a method for the photon-counting detection of x-ray radiation using direct conversion detectors, whereby:

as a function of the existing radiation energy, current and/or voltage pulses which are largely proportional hereto are generated and the generated current and/or voltage pulses are counted in the detector when a predetermined current and/or voltage threshold is exceeded, and a threshold is used as a predetermined current and/or voltage threshold, which corresponds to a detection of a photon with an energy, which is lower than the k-edge of the detector material used.

It is particularly advantageous here if the used threshold is simultaneously greater than the existing noise level in the measuring system.

With respect to concrete values, it is proposed to set the threshold such that it corresponds to an incident photon of less than 23 keV, preferably less than 20 keV, preferably less than 10 keV, preferably between 10 keV and 5 keV.

It is also proposed that a continually operating pulse height discriminator or a pulse height discriminator operating in clocked mode is used for measurement purposes. It is particularly favorable however if a combination of two logically linked operating pulse height discriminators is used to measure radiation, whereby at least one continuously operating pulse height discriminator and at least one pulse height discriminator operating in clocked mode are used.

Furthermore, measures for reducing or even minimizing the noise of the evaluation electronics system can be embodied in the detector.

With respect to improving or even optimizing the energy resolution of the detector including a plurality of detector elements, it is favorable to use the same threshold for all detector elements, whereby it is particularly favorable to use an individual threshold for each detector element for the maximum reduction of a drift of the response behavior of the detector including a plurality of detector elements.

Within the scope of at least one embodiment of the invention, a detector system is also proposed for the photon-counting detection of x-ray radiation with direct conversion detector elements, whereby the detector elements and their evaluation electronics systems are to be embodied such that the afore-described inventive method is executed.

FIG. 1 shows the course of the drift of an example counting detector of the set count threshold or response threshold. To this end, the count threshold is plotted on the x-coordinate as an equivalent to the photon energy incident in the detector in keV and the percentual deviation of the resulting count rate is shown on the y-coordinate compared with the actual photon events. The course of this dependency is indicated by the curve shown in the diagram. As apparent from the course, a double peak at approximately 60 keV and 70 keV shows, in a relatively high energy range, the influence of the characteristic radiation of the x-ray tubes used, whereas the influence of the k-lines of the detector material is shown in the region between 20 keV and 30 keV. It is therefore particularly favorable to place the count threshold of the detector under this influence of the k-lines of the respective detector material, certainly above the energy level of the noise. To achieve an adequately large noise level range here, it is particularly favorable to take corresponding measures to ensure that the noise level is as low as possible.

Figure 2:
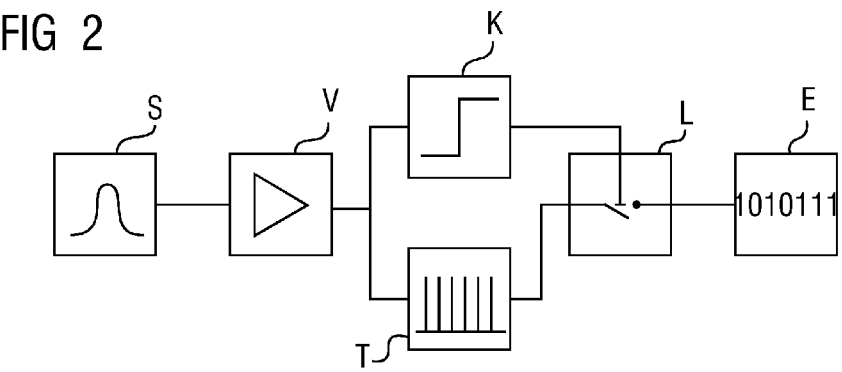
FIG. 2 shows a circuit arrangement of a detector electronics system having a counting and continuous counter.

An example switching electronics system of a counting detector is shown in FIG. 2. The count pulses are fed here from the left to a pulse shaper S with an amplifier V arranged downstream thereof. The shaped and amplified signals are then routed in parallel to a continuous pulse height discriminator (=counter) K and a clocked pulse height discriminator (=counter) T. In accordance with an embodiment of the invention, these pulse height discriminators are set with respect to their threshold value such that this corresponds to a lower energy than the energy of the k-edge of the used detector material. The outputs of the continuous pulse height discriminator K and the clocked pulse height discriminator T are then linked by way of a logic element L such that as linear a shared counted result E as possible exists in the result.

Figure 3:
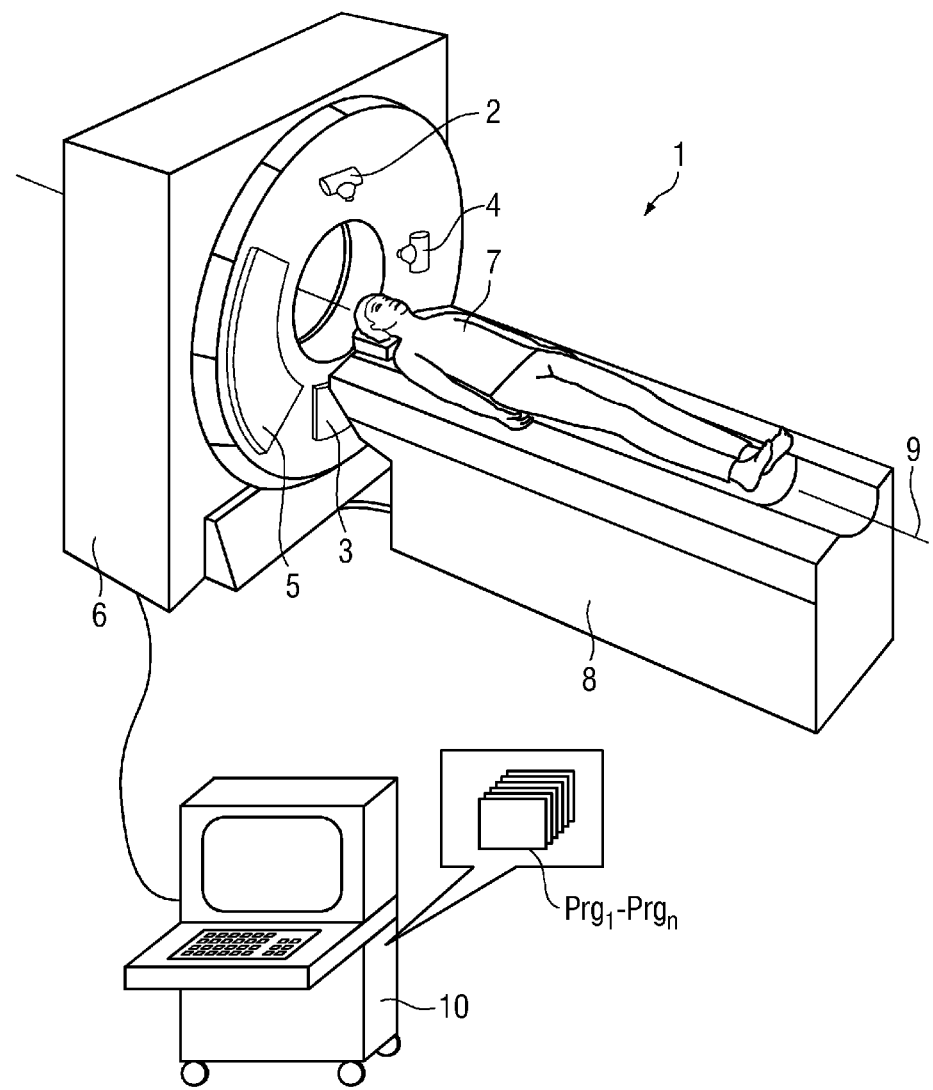
FIG. 3 shows a CT system.

An embodiment of the inventive method can be used in conjunction with any detectors with counting detector elements, for instance direct conversion semiconductor materials. A computed tomography system with inventively embodied detectors is only shown here in FIG. 3 by way of example. This CT system 1 comprises a gantry housing 6, in which a gantry is located with a radiation source 2, which rotates about a system axis 9 together with an opposite detector 3. Optionally, at least one second radiation source 4 and an opposite detector 5 can be arranged on the gantry. For scanning purposes, a patient 7 on a patient couch 8 is moved through the measurement field for instance, while the radiation sources 2, 4 and detectors 3, 5 on the gantry rotate about the system axis 9.

The signals detected by the detector 3 and/or 5 can be processed directly in an inventively embodied and/or adjusted detector electronics system or correspondingly amplified in a central computing station 10. Computer programs Prg1-Prgn can also be stored there, which inter alia implement an embodiment of the inventive method during operation.

Reference is made to an embodiment of the inventive method and an embodiment of the inventive circuit arrangement not being restricted to tomographic applications, but instead being useable with each particle or photon-detecting detector with counting detector elements.

It is evident that the afore-cited features of the invention cannot only be used in the respectively specified combination but instead also in other combinations or alone without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for photon-counting detection of x-ray radiation using at least one direct conversion detector, the method comprising:
   generating at least one of current and voltage pulses as a function of existing radiation energy;
   selecting at least one energy threshold based on a k-edge of detector material in the at least one detector such that the at least one energy threshold is less than the k-edge of the detector material, the at least one energy threshold being one of a current energy threshold and a voltage energy threshold; and
   counting the generated at least one pulses in the at least one detector upon the at least one energy threshold being exceeded.

2. The method as claimed in claim 1, wherein the energy threshold is greater than an existing noise level in a measuring system including the at least one detector.

3. The method as claimed in claim 1, further comprising:
   measuring the existing radiation using a continuously operating pulse height discriminator.

4. The method as claimed in claim 1, further comprising:
   measuring the existing radiation using a pulse height discriminator operating in clocked mode is used for measurement of radiation.

5. The method as claimed in claim 1, further comprising:
   measuring the existing radiation using a combination of at least two logically linked pulse height discriminators, wherein the at least two logically linked pulse height discriminators include at least one continuously operating pulse height discriminator and at least one pulse height discriminator operating in clocked mode.

6. The method as claimed in claim I, wherein the at least one detector includes measures to minimize noise of an evaluation electronics system.

7. The method as claimed in claim I, wherein, in order to optimize an energy resolution of the at least one detector including a plurality of detector elements, the energy threshold is common for all of the plurality of detector elements.

8. The method as claimed in claim 1, wherein, in order to maximally reduce a drift of a response behavior of the at least one detector including a plurality of detector elements, the energy threshold is one of a plurality of separate energy thresholds used for each of the plurality of detector elements.

9. A non-transitory computer readable medium including program segments for, when executed on a computer device, causing the computer device to implement the method of claim 1.

10. The method as claimed in claim 1, wherein the at least one detector includes a plurality of pixels, and the energy threshold for each pixel is further based on dark count rate criteria.

11. The method as claimed in claim 1, wherein the energy threshold is between 10 keV and 20 keV.

12. A detector system for photon-counting detection of x-ray radiation, comprising:

a plurality of direct conversion detector elements; and an evaluation electronics system configured to, generate at least one of current and voltage pulses as a function of existing radiation energy, select at least one energy threshold based on a k-edge of detector material in the at least one detector such that the at least one energy threshold is less than the k-edge of the detector material, the at least one energy threshold being one of a current energy threshold and a voltage energy threshold, and count the generated at least one of current and voltage pulses in at least one of the detector elements upon the at least one energy threshold being exceeded.

13. The method as claimed in claim 12, wherein the threshold is set such that it corresponds to an incident photon of less than 10 keV.

14. The method as claimed in claim 13, wherein the threshold is set such that it corresponds to an incident photon of between 10 keV and 5 keV.

15. The detector system as claimed in claim 12, wherein the evaluation electronics system includes a continuously operating pulse height discriminator configured to measure the existing radiation.

16. The detector system as claimed in claim 12, wherein the evaluation electronics system includes a pulse height discriminator configured to operate in clocked mode to measure the existing radiation.

17. The detector system as claimed in claim 12, wherein the evaluation electronics system includes a combination of at least two logically linked pulse height discriminators configured to measure the existing radiation, wherein the at least two logically linked pulse height discriminators include at least one continuously operating pulse height discriminator and at least one pulse height discriminator operating in clocked mode.

18. The detector system as claimed in claim 12, wherein the energy threshold is between 10 keV and 20 keV.

19. A detector system for photon-counting detection of x-ray radiation, comprising:

a plurality of direct conversion detector elements; and an evaluation electronics system configured to, generate at least one of current and voltage pulses as a function of existing radiation energy, select at least one energy threshold based on i) a desired detector drift, and ii) K-edge of detector material in the at least one detector such that the at least one energy threshold is less than the K-edge of the detector material, the at least one energy threshold being one of a current energy threshold and a voltage energy threshold, and count the generated at least one of current and voltage pulses in at least one of the detector elements upon the at least one energy threshold being exceeded.

20. The detector system as claimed in claim 19, wherein the energy threshold is between 10 keV and 20 keV.

\* \* \* \* \*